United States Patent
Herbst et al.

[11] Patent Number: 5,637,689
[45] Date of Patent: Jun. 10, 1997

[54] PROCESS FOR THE PREPARATION OF ALKYLIMIDAZOLIDONE (METH) ACRYLATE(S)

[75] Inventors: Gilles Herbst, Spicheren; Alain Riondel, Forbach, both of France

[73] Assignee: Elf Atochem S.A., Puteaux, France

[21] Appl. No.: 223,608

[22] Filed: Apr. 6, 1994

[30] Foreign Application Priority Data

Apr. 6, 1993 [FR] France ................... 93 04067

[51] Int. Cl.⁶ .............. C07D 233/02; C07D 239/04; C07D 243/04; C07D 245/02
[52] U.S. Cl. ............... 540/460; 540/492; 544/318; 548/324.1
[58] Field of Search ............... 540/460, 492; 544/318; 548/324.1

[56] References Cited

U.S. PATENT DOCUMENTS

| | | | |
|---|---|---|---|
| 4,202,990 | 5/1980 | Murakami et al. | 560/217 |
| 4,777,265 | 10/1988 | Merger et al. | 548/320 |
| 5,210,199 | 5/1993 | Grosius et al. | 548/324.1 |

*Primary Examiner*—Mukund J. Shah
*Assistant Examiner*—King Lit Wong
*Attorney, Agent, or Firm*—Millen, White, Zelane, & Branigan, P.C.

[57] ABSTRACT

A compound (I) is prepared by reaction of at least one (meth) acrylate (II) with a heterocyclic alcohol (III), in the presence of at least one catalyst chosen from the chelates of calcium with 1,3-dicarbonyl compounds, such as calcium acetylacetonate.

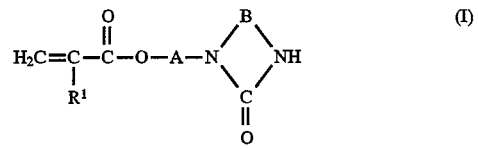

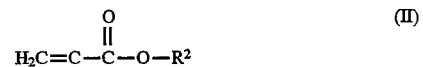

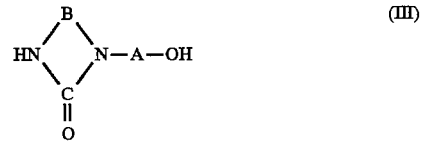

$R^1$=H, $CH_3$; A, B=$C_2$–$C_5$ alkylene; $R^2$=$C_1$–$C_4$ alkyl.

12 Claims, No Drawings

PROCESS FOR THE PREPARATION OF ALKYLIMIDAZOLIDONE (METH) ACRYLATE(S)

The present invention relates to a process for the manufacture of a compound of formula:

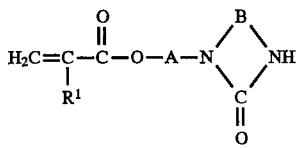

in which:

R$^1$ represents hydrogen or methyl; and

A and B each independently represent an alkylene group containing a straight or branched chain, having from 2 to 5 carbon atoms, by reaction of at least one (meth) acrylate of formula:

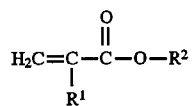

in which:

R$^1$ has the above meaning; and

R$^2$ represents a C$_1$–C$_4$ alkyl group, with a hetero-cyclic alcohol of formula:

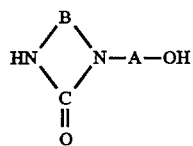

in which A and B have the above meanings.

These compounds of formula (I) are known for their role in the constitution of polymers which are useful as coatings and adhesives, for treating paper and textiles, in particular from U.S. Pat. US-A-2, 871, 223, as well as for their uses as agents for treating leather, and in the production of emulsion paints. Ethylimidazolidone methacrylate (EIOM) is mainly used as a wet adhesion promoter.

In the process defined above, which is known from European Patent Application EP-A-0,236,994, the catalysts are chosen from titanium alcoholates such as tetraalkyl titanates, and chelates of Ti, Zr, Fe or Zn with 1,3-dicarbonyl compounds, such as acetylacetonates of Ti, Zr, Fe or Zn.

It is also known, from European Patent Application EP-A-0,433,135, to use as catalysts, for this same reaction, dialkyltin oxides, tin dialkyl dialkoxides and tin dialkyl diesters. Di-n-butyltin oxide (DBTO) may be mentioned among others. The reaction carried out with such catalysts is selective and may be transferred to the industrial scale.

However, in the particular case of the synthesis of EIOM, it is sought to achieve the most complete possible conversion of hydroxyethylimidazolidone (HEIO) which, in the case of a catalysts by DBTO, requires a temperature level of at least 103° C., which is hardly compatible with the low thermal stability of the reaction medium.

It has thus been sought to find a catalyst other than DBTO and the analogous catalysts, which allows a lower temperature level. It has now been discovered that the use of a chelate of calcium with a 1,3-dicarbonyl compound, in particular calcium acetylacetonate (Ca(acac)2), or of such a chelate mixed with at least one among the dialkyl oxides, dialkyl dialkoxides and dialkyl diesters of tin, makes it possible to perform the process at a temperature lower than 100° C. (95° C.–96° C. in particular), while at the same time leading to comparable results from the point of view of the yield of EIOM and of the conversion of HEIO.

The subject of the present invention is thus the process for the manufacture of a compound of formula (I), as has been defined above, in the presence of at least one catalyst chosen from the chelates of calcium with 1,3-dicarbonyl compounds.

By way of examples of dicarbonyl compounds, there may be mentioned an ester of a β-keto acid, such as the acetylacetic ester, or a 1,3-diketone such as acetyl-acetone, 3-methylacetylacetone, benzoylacetone, dibenzoylmethane, 2,4-hexanedione, 3,5-heptanedione, 3-phenylacetylacetone, 4,4,4-trifluoro-1-phenyl- 1,3-butanedione, 2,2,6,6-tetramethyl-3,5-heptanedione, 1,1,1-trifluoro-5,5-dimethyl-2,4-hexanedione and 1,1,1-trifluoro-2,4-pentanedione. In particular, calcium acetylacetonate may be mentioned as a useful catalyst according to the invention.

As examples of reactants of formula (II), there may in particular be mentioned methyl, ethyl, n-propyl, isopropyl, n-butyl and isobutyl acrylates and methacryl- ates.

As an example of a heterocyclic alcohol of formula (III), there may in particular be mentioned 1-(2-hydroxyethyl)-2-imidazolidone (HEIO).

The amount of catalyst(s) used for the implementation of the process according to the invention is generally between approximately 0.05% and 2% in moles preferably between approximately 0.1 and 1 mol%, per mole of heterocyclic alcohol of formula (III).

Moreover, there may advantageously be used at least one additional catalyst chosen from the dialkyl oxides, dialkyl dialkoxides and dialkyl diesters of tin, in particular di-n-butyltin oxide (DBTO). The amount of additional catalyst(s) is the same as that indicated for the catalyst(s) of calcium chelate type.

The reaction of the process according to the invention may be carried out in the presence of an excess of one or other of the reactants. It is, however, recommended that the (meth) acrylate of formula (II) heterocyclic alcohol of formula (III) molar ratio is approximately between 1.1 and 7.0, preferably between 2.0 and 6.0. By performing the process with a large molar excess of (meth) acrylate relative to the heterocyclic alcohol, there is obtained, on conclusion of the reaction, a solution of the compound of formula (I) in the (meth) acrylate which may be used directly for certain applications, such as for obtaining paints and coatings or alternatively for treating leather.

The reaction of the process according to the invention is preferably carried out in the presence of at least one polymerization inhibitor, which is used, for example, in an amount of 0.05 to 0.5% by weight based on the weight of the heterocyclic alcohol of formula (III). As examples of polymerization inhibitors which may be used, there may in particular be mentioned phenothiazine, hydroquinone methyl ether, di-tert-butylcatechol, hydroquinone, p-anilinophenol, para-phenylenediamine and their mixtures in all proportions.

The reaction of the process according to the invention is preferably carried out under a pressure which does not exceed atmospheric pressure, for example a pressure between 0.3 and 1 bar. The reaction is advan- tageously performed under a stream of air bubbles. It is carried out by mixing the (meth) acrylate of formula (II) and the heterocyclic alcohol of formula (III), and by heating the reaction mixture to reflux, generally at a temperature approximately between 85 and 100° C., this temperature obviously being dependent on the exact nature of the alcohol and of the (meth) acrylate, and on the catalytic system used.

In the implementation of the process according to the invention, it is recommended to achieve a maximum dehydration before adding the catalyst, so as to avoid deactivation of the latter by water. This result may, for example, be arrived at by heating the initial mixture of (meth) acrylate of formula (II), of heterocyclic alcohol of formula (III) and of polymerization inhibitor to reflux, followed by separating the azeotrope of (meth)- acrylate and water by distillation. At this stage, after separation of the distillate and after sufficient cooling of the reaction mixture to condense all of the vapours in the column, the catalyst(s) is (are) introduced into the reaction mixture.

The duration of the reaction according to the invention, which obviously depends on the reaction conditions, such as the temperature, pressure and the amount of catalyst(s) used, is generally approximately between 1 and 10 hours. It also obviously depends on the nature of the reactants used.

The reaction mixture is thus heated to reflux until the temperature at the head reaches the distillation temperature of the azeotrope of the (meth) acrylate and the alcohol of formula $R_2OH$ formed by the reaction. This distillation temperature is approximately 65° C. for the azeotrope of methanol and methyl methacrylate, approximately 82° C. for the azeotrope of ethanol and ethyl methacrylate, and approximately 84° C. for the azeotrope of ethanol and ethyl acrylate. Regardless of the compounds present in the column, the head temperature must be maintained below approximately 120° C., if need be by using a reduced pressure, in order to avoid any risk of polymerization.

The possible excess (meth) acrylate may subsequently be removed by evaporation, so as to isolate the compound of formula (I) from the reaction medium, generally in the solid state: thus, 1-(2-hydroxyethyl)- 2-imidazolidone acrylate is a white crystalline solid of melting point equal to 43° C., which is soluble under cold conditions in ketches, alcohols, aromatic hydrocarbons and water, insoluble under cold conditions in saturated hydrocarbons and which precipitates at 0° C. in ethyl acrylate. 1-(2-Hydroxyethyl)imidazolidone methacrylate is a white crystalline solid of melting point equal to 47° C., having the same solubility properties as the above product. On conclusion of the evaporation procedure, the solid crystalline product may in addition be purified by washing with a light alcohol such as methanol, and/or with a petroleum ether, followed by filtration and drying.

Isolation of the compound (I) may also be carried out by partial evaporation of the (meth) acrylate, followed by crystallization at a sufficiently low temperature (preferably lower than or equal to 0° C.) and for a sufficiently long period (which may reach up to 15 hours), and then filtration, followed by the purification steps described above.

Finally, a third method for isolating the compound of formula (I) from the solution containing it consists in carrying out an extraction with water, followed by a separation of the phases, an evaporation of the (meth) acrylate and the purification steps described above.

The examples which follow illustrate the invention without, however, limiting it. In these examples, the percentages are indicated by weight, except where otherwise indicated.

Example 1 (Comparative) and Examples 2 to 17 of the invention:

General procedure

Into a glass jacketed reactor which is equipped with a probe for measuring the temperature (at the foot), a variable speed mechanical stirrer and a packed adiabatic column, and is surmounted with a reflux head, are introduced 130 g of HEIO and 560 g of MMA, as well as 0.12 g of phenothiazine (PTZ) and 0.15 g of hydroquinone methyl ether (HQME) as stabilizers. A means of stabilizing the head of the column was set up using a 0.1% solution of HQME in MMA. The contents of the reactor are brought to reflux for 1 hour, at a temperature at the head of the column of 98°–100° C. and a temperature at the foot of the column lower than or equal to 100° C., so as to remove the MMA-water azeotrope.

The catalyst(s) is (are) subsequently introduced into the reactor in the amount indicated, as well as the amount of MMA necessary to obtain an MMA/HEIO molar ratio =5.2. The pressure is adjusted to maintain in the reactor a temperature indicated by T° C. in the table below. The removal of the MMA/MeOH azeotrope is regulated by a set head temperature (boiling point of the azeotrope +2° C.). When the amount of methanol removed corresponds to the expected amount, the reaction is continued until no further formation of methanol is observed (head temperature =boiling point of MMA), at total reflux, at the pressure under consideration.

After cooling, the crude EIOM is recovered, assaying at 30–40% of EIOM.

The yield of EIOM and the conversion of HEIO are determined from the analysis by HPLC liquid phase chromatography of the crude reaction product, by the following equations:

$$\text{Conversion } HEIO\ (\%) = \frac{(\text{starting } HEIO - \text{final } HEIO)}{\text{starting } HEIO} \times 100$$

$$\text{Yield of } EIOM\ (\%) = \frac{\text{Number of moles of } EIOM \text{ formed}}{\text{Number of moles of starting } HEIO} \times 100$$

The results for the various tests carried out are reported in the table below.

TABLE

| Example | Catalyst and mol % of catalyst relative to HEIO | | (°C.) | Time (h) | Remaining HEIO (%) | Conversion HEIO (%) | Yield EIOM (%) |
|---|---|---|---|---|---|---|---|
| 1 (Comparative) | DBTO | 0.8 | 96 | 7 | 2.5 | 91 | 84.3 |
| 2 | Ca(acac)$_2$ | 0.2 | 96 | 7 | 1.8 | 89.3 | 84.5 |
| 3 | Ca(acac)$_2$ | 0.4 | 96 | 6.5 | 1 | 96.3 | 89.4 |
| 4 | Ca(acac)$_2$ | 0.6 | 96 | 6 | 0.5 | 98.2 | 79.6 |
| 5 | Ca(acac)$_2$ | 0.4 | 100 | 5 | 0.22 | 99.3 | 75.4 |
| 6 | Ca(acac)$_2$ | 0.2 | 100 | 6 | 0.26 | 99.2 | 74.8 |
| 7 | Ca(acac)$_2$ | 0.6 | 96 | 7 | 1 | 96 | 85 |
| 8** | Ca(acac)$_2$ | 0.4 + 0.2 | 96 | 6 | 0.7 | 97 | 83 |

TABLE-continued

| Example | Catalyst and mol % of catalyst relative to HEIO | | (°C.) | Time (h) | Remaining HEIO (%) | Conversion HEIO (%) | Yield EIOM (%) |
|---|---|---|---|---|---|---|---|
| 9 | Ca(acac)$_2$ | 0.5 | 96 | 7 | 0.65 | 97.4 | 77 |
| 10 | Ca(acac)$_2$ | 0.4 | 96 | 7.5 | 0.64 | 97.6 | 86 |
| 11 | Ca(acac)$_2$ | 0.2 + DBTO 0.6 | 96 | 7 | 2.2 | 92.8 | 91 |
| 12 | Ca(acac)$_2$ | 0.4 + DBTO 0.4 | 96 | 7 | 0.3 | 98.9 | 92.9 |
| 13 | Ca(acac)$_2$ | 0.1 + DBTO 0.7 | 96 | 6 | 1.2 | 97.8 | 93.3 |
| 14 | Ca(acac)$_2$ | 0.3 + DBTO 0.6 | 96 | 6 | 0.37 | 98.7 | 85 |
| 15* | Ca(acac)$_2$ | 0.1 + DBTO 0.6 | 96 | 7.5 | 1 | 95 | 92 |
| 16* | Ca(acac)$_2$ | 0.2 + DBTO 0.6 | 96 | 7 | 0.7 | 97 | 85.5 |
| 17 | Ca(acac)$_2$ | 0.4 + DBTO 0.4 | 96 | 7.5 | 0.6 | 97 | 88.4 |

*Addition of the catalyst containing calcium in 2 portions, the second addition being carried out when the extent of the reaction process is approximately 90%
**Addition of a further 0.2% of catalyst at the end of the synthesis The comparative examination of this table shows the advantage of preferentially using Ca(acac)$_2$ and Ca(acac)$_2$ +DBTO relative to DBTO for the synthesis of EIOM:

lower reaction temperature, hence greater safety and better control of the process;

values for the yield of EIOM and for the conversion of HEIO which are better than those obtained with DBTO.

We claim:

1. A process for the manufacture of a compounds of formula:

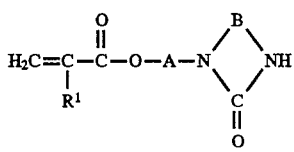

in which:

R$^1$ represents hydrogen or methyl; and

A and B each independently represent an alkylene group containing a straight or branched chain, having from 2 to 5 carbon atoms, by reaction of at least one (meth) acrylate of formula:

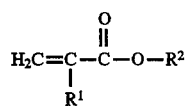

in which:

R$^1$ has the above meaning; and

R$^2$ represents a C$_1$–C$_4$ alkyl group, with a heterocyclic alcohol of formula:

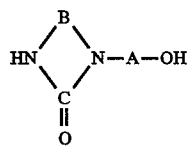

in which A and B have the above meanings, in the presence of a catalytic quantity of (A) at least one chelate of calcium with 1,3-dicarbonyl compound and (B) at least one tin-containing catalyst selected from the group consisting of a dialkyltin oxide, a tin dialkyl dialkoxide and a tin dialkyl diester.

2. A process according to claim 1, characterized in that di-n-butyltin oxide is tin-containing catalyst.

3. A process according to claim 1 characterized in that the amount of said tin-containing catalyst(s) used is from 0.05 to 2% in moles per mole of heterocyclic alcohol of formula (III).

4. A process according to claim 1, wherein both (A) and (B) are each used in an amount of from 0.05% to 2% in moles per mole of heterocyclic alcohol of formula (III).

5. A process according to claim 1, characterized in that the reaction is carried out at a temperature between 85° and 100° C. and compound I is ethylimidazolidone methacrylate.

6. A process according to claim 1, characterized in that there is used a molar ratio of the (meth)acrylate of formula (II) to the heterocyclic alcohol of formula (III) which is between 1.1 and 7.0.

7. A process according to claim 1, characterized in that the reaction is carried out for a period between 1 and 10 hours, under a pressure of 0.3 to 1 bar.

8. A process according to claim 1, characterized in that the reaction is carried out in the presence of at least one polymerization inhibitor chosen from phenothiazine, hydroquinone methyl ether, di-tertbutylcatechol, hydroquinone, p-anilinophenol, paraphenylenediamine and their mixtures in all proportions.

9. A process according to claim 1, wherein the reaction is conducted at 85°–100° C.

10. A process according to claim 1, wherein the reaction temperature is 95°–96° C.

11. A process according to claim 1, wherein said at least one tin-containing catalyst is di-n-butyltin oxide and said chelate of calcium with a 1,3-dicarbonyl compound is calcium acetyl acetonate.

12. The process of claim 1, wherein the reaction is conducted at a temperature lower than 100° C.

* * * * *